US00PP30543P3

(12) United States Plant Patent
Moon

(10) Patent No.: US PP30,543 P3
(45) Date of Patent: May 28, 2019

(54) ELM TREE NAMED 'UAMTF'

(50) Latin Name: *Ulmus alata*
Varietal Denomination: UAMTF

(71) Applicant: SOUTHERN SELECTIONS, LLC, Loganville, GA (US)

(72) Inventor: Dwayne C. Moon, Logansville, GA (US)

(73) Assignee: Southern Selections, LLC, Logansville, GA (US)

( * ) Notice: Subject to any disclaimer, the term of this patent is extended or adjusted under 35 U.S.C. 154(b) by 0 days.

(21) Appl. No.: 15/731,948

(22) Filed: Aug. 28, 2017

(65) Prior Publication Data

US 2019/0069459 P1 Feb. 28, 2019

(51) Int. Cl.

| | |
|---|---|
| ***A01H 5/00*** | (2018.01) |
| ***A01H 6/00*** | (2018.01) |
| ***A01H 5/04*** | (2018.01) |

(52) U.S. Cl.
USPC ..... Plt./221
CPC ..... *A01H 6/00* (2018.05); *A01H 5/04* (2013.01)

(58) Field of Classification Search
USPC ..... Plt./216, 221
See application file for complete search history.

*Primary Examiner* — Susan McCormick Ewoldt
*Assistant Examiner* — Karen M Redden
(74) *Attorney, Agent, or Firm* — Stinson Leonard Street LLP

(57) ABSTRACT

A new and distinct variety of Winged Elm tree named 'UAMTF' substantially as herein shown, illustrated and described, characterized particularly as to novelty by its strong central leader as well as the refined, graceful branching which is attained through minimal and insignificant cork-like wings in comparison to the heavy wings evident in seedling Winged Elm. These form differences, along with its resistance to the powdery mildew and other leaf-borne illnesses found in seedling Winged Elm makes my selection uniquely different from all known patent selections and seedlings.

10 Drawing Sheets

Latin name of genus and species: *Ulmus alata.*
Varietal denomination: Winged Elm tree which I have named 'UAMTF'.

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a new and distinct variety of Winged Elm tree (*Ulmus alata*), which I have named 'UAMTF'.

Discovery

The new *Ulmus alata* is a product of chance discovery. The new variety 'UAMTF' is the result of a selection made by the inventor, Dwayne Moon, from an *Ulmus alata* found in the wild in October of 2007 from a field in Oconee County, Ga. Evaluation of this tree continues in a field in Oconee County, Ga.

Propagation

'UAMTF' was asexually propagated by grafting softwood cuttings at the direction of Dwayne Moon from May 1st through Aug. 1, 2008 in Loganville, Walton County, Ga. The propagation process is done by selecting actively growing shoot tips, taking cuttings, and applying rooting hormones (K-IBA at 3000 ppm) with intramural mist every 10 minutes for 30 seconds with a 30% increase after rooting in mist duration every day on and off until cuttings are weaned off to daily water regiment. Initial rooting takes place in three to four weeks. This propagation from rooted cuttings results in a progeny which has proven the characteristics of my new variety to be genetically stable. Furthermore, these observations have confirmed that my new variety represents a new and improved variety of Winged Elm tree as particularly evidenced by the its minimal and insignificant cork-like wings on the branches as well as its vase-like shape with a strong central leader. It is also disease resistant to the powdery mildew and other leaf-borne illnesses found in seedling Winged Elm. These genetic traits can be consistently reproduced by asexual propagation.

Uniqueness

'UAMTF' was a chance discovery found in a field (unknown *Ulmus alata* parents) in Oconee, Ga. I claim that the genetic characteristics of this tree are the result of naturally occurring cross-pollination. The characteristics of my new tree distinguish it from other typical seedling Winged Elm trees and the known cultivars. At the time this tree was selected, I observed 'UAMTF' Winged Elm as a 10 inch caliper tree exhibiting pyramidal growth habit with a strong central leader along with minimal and insignificant cork-like wings on the branches. Seedling Winged Elm has extensive and wide-spread cork-like wings appearing on opposite sides of twigs and branches along with a variable form canopy from pyramidal to vase or rounded with pendulous branches. 'UAMTF' Winged Elm is also disease resistant to the powdery mildew and other leaf-borne illnesses found in seedling Winged Elm.

Use

'UAMTF' was observed for a period of 10 years and is believed to be particularly useful as a specimen tree in commercial and residential areas, for street tree planting and in large areas such as golf courses, commercial sites and parks as well as meeting native species requirements for urban forest and municipality requirements. 'UAMTF" will also benefit growers who will profit from the desired look of a high quality tree due to its strong central leader as well as the refined, graceful branching which is attained through minimal and insignificant cork-like wings in comparison to the heavy wings evident in seedling Winged Elm. It has also proven to be disease resistant to the powdery mildew and other leaf-borne illnesses found in seedling Winged Elm.

SUMMARY OF THE INVENTION

Background

Seedling Winged Elm has a variable form canopy from pyramidal to vase or rounded with pendulous branches. It is most easily recognized by the very broad, thin pair of corky wings that form along the branchlets after a couple of years. Mature native Winged Elm trees are medium-sized, 40 to 50 feet in height with a spread of 30 to 40 feet; some native specimens can reach 90 feet or more in height. In nursery settings, Winged Elm trees often require a significant amount of effort to maintain a central leader. My Winged Elm tree 'UAMTF' is an improvement over the species in that it has a pyramidal growth habit with a strong central leader as well as the refined, graceful branching which is attained through minimal and insignificant cork-like wings in comparison to seedling Winged Elm. It is also disease resistant to the powdery mildew and other leaf-borne illnesses found in seedling Winged Elm.

Winged Elm is native to the southeastern corner of the United States, from southern Virginia west to the Ohio valley and Texas, and south into Florida. Winged Elm adapts well to both dry, gravely soils or moist, well-drained areas. They are commonly found in upland woods and flood plains. Growth rate is often very slow, the trunk increasing in diameter by less than 5 mm (3/16 in) per year. It has a green leaf in summer changing to yellow in the fall. My new cultivar differs from the species in that it is asexually propagated by the method of rooted cuttings which creates a pyramidal growth habit with a strong central leader as well having minimal and insignificant cork-like wings in comparison to that of seedling Winged Elm. It has also proven to be resistant to the powdery mildew and other leaf-borne illnesses found in Winged Elm. The ultimate height and width of 'UAMTF' is not known. I expect my new variety of Winged Elm tree 'UAMTF' to perform as well as the species.

Industry Representation

Cultivated Winged Elm tree is predominantly represented in the industry by seedling material reproduced sexually through seed production and seedling establishment with some cultivars. This accounts for a high degree of variability in the industry, both in the landscape and nursery. Seedling Winged Elm tree is variable in growth rate, habit, and leaf characteristics, and overall consistency is difficult to maintain in a production system.

The *Manual of Woody Landscape Plants* ($6^{th}$ ed.) lists one known Winged Elm cultivar which is known as 'Lace Parasol' (not patented). The present cultivar 'UAMTF' differs from 'Lace Parasol' in that 'Lace Parasol' is usually grafted onto either *Ulmus alata* or *Ulmus parvifolia* rootstock, has a weeping shape with a height of 8 to 12 feet and a width of 10 to 15 feet along with heavy cork-like wings. 'UAMTF' is asexually reproduced with pyramidal growth habit with a strong central leader, has an approximate height of 30' and a width of 20', as well as the refined, graceful branching which is attained through minimal and insignificant cork-like wings with a disease resistance to the powdery mildew. These differences make my selection uniquely different from all known patent selections and seedlings.

BRIEF DESCRIPTION OF THE DRAWINGS

The accompanying photographs depict the color of the tree and foliage of my new Winged Elm tree as nearly as is reasonably possible to make the same in a color illustration of this character.

DETAILED DESCRIPTION OF THE INVENTION

Botanical Description of the Plant

Figure 1:
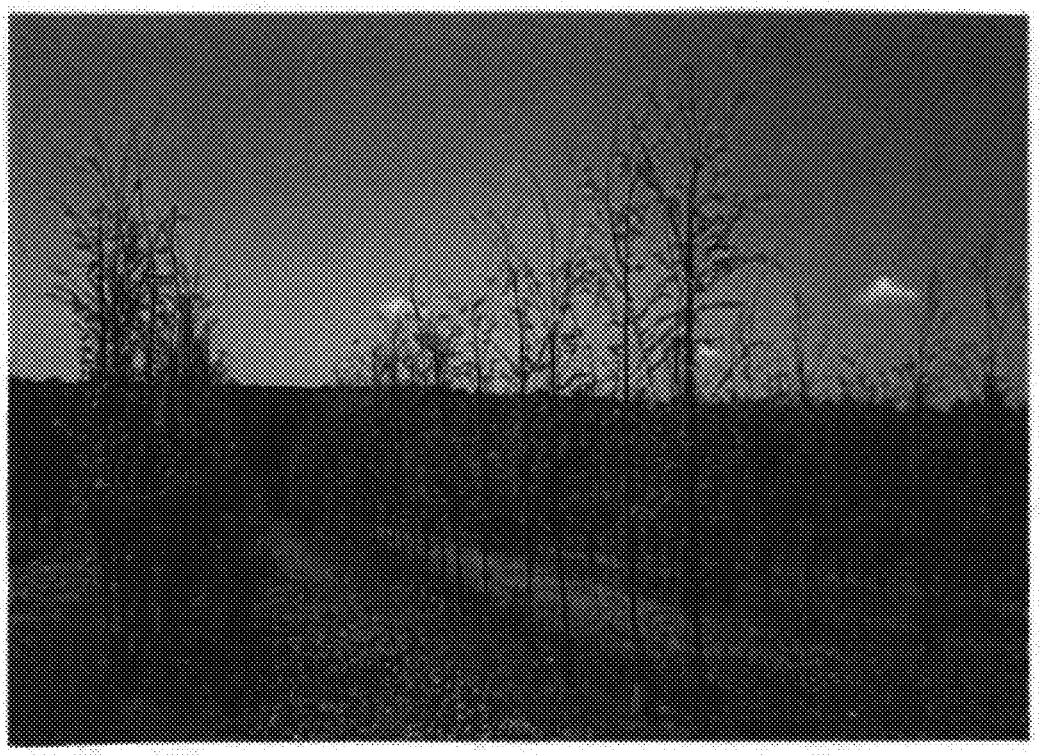
FIG. 1 shows a selection taken in the wild from a field in Oconee County, Ga. in October of 2007.
Figure 2:
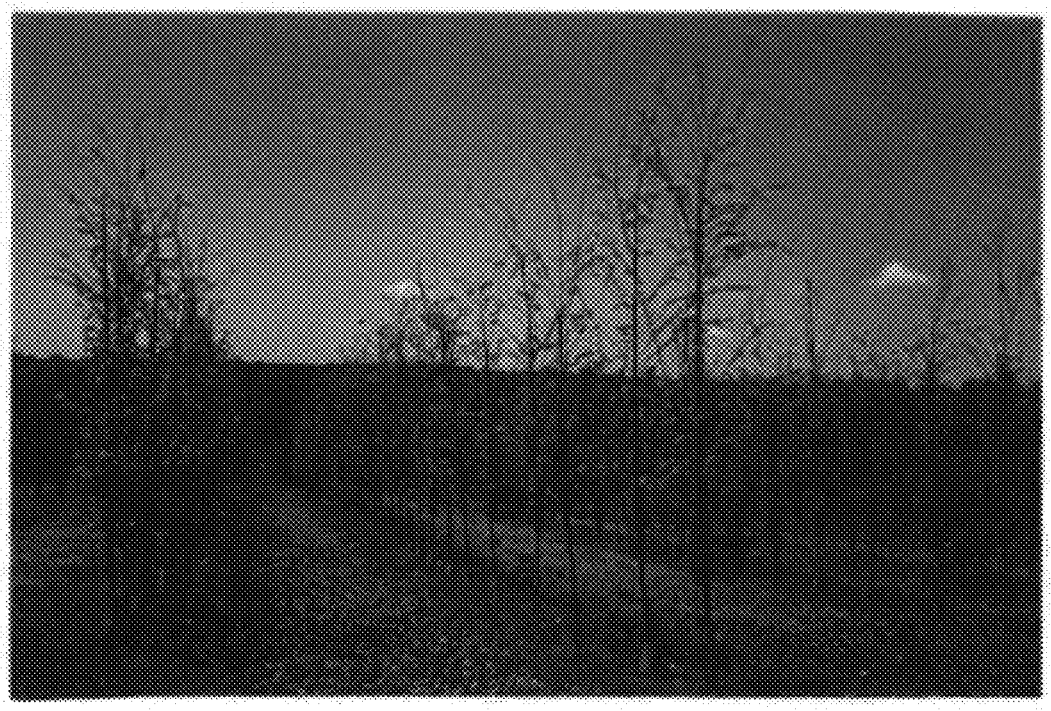
FIG. 2 taken of a field block shows the progeny of my new variety.
Figure 3:
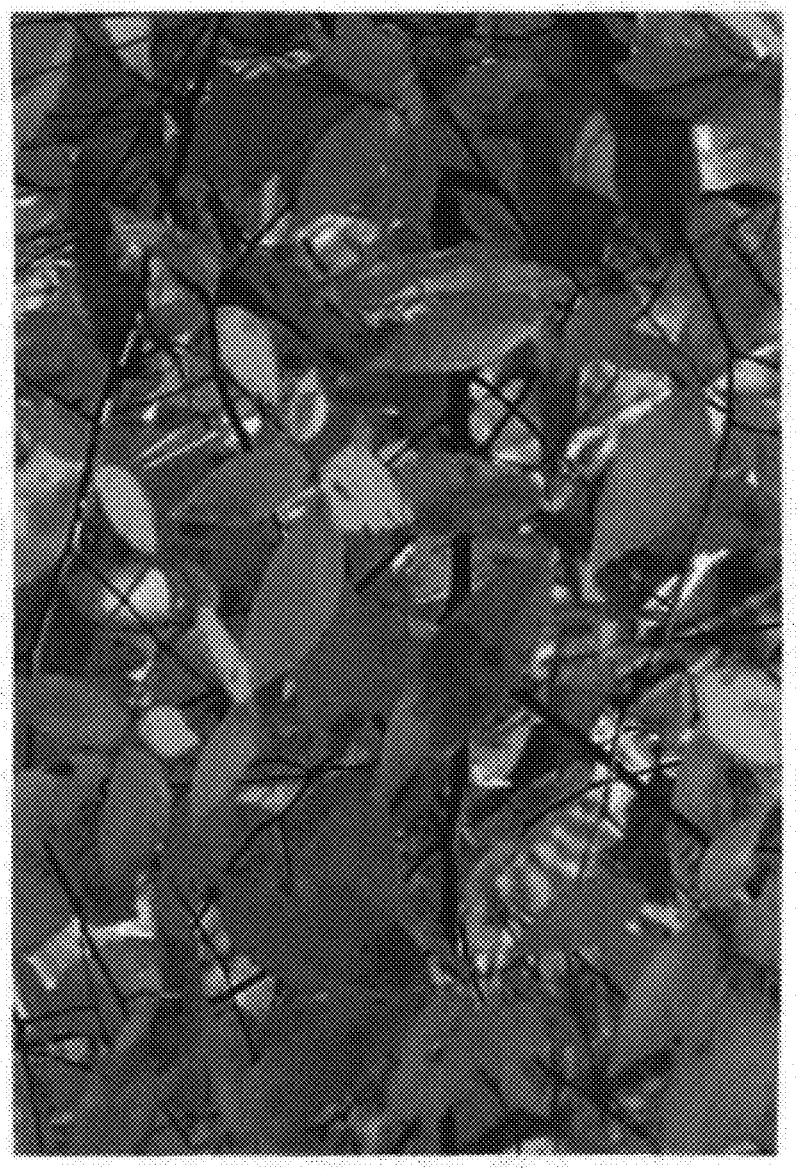
FIG. 3 shows the overall fall color of the claimed cultivar.
Figure 4:
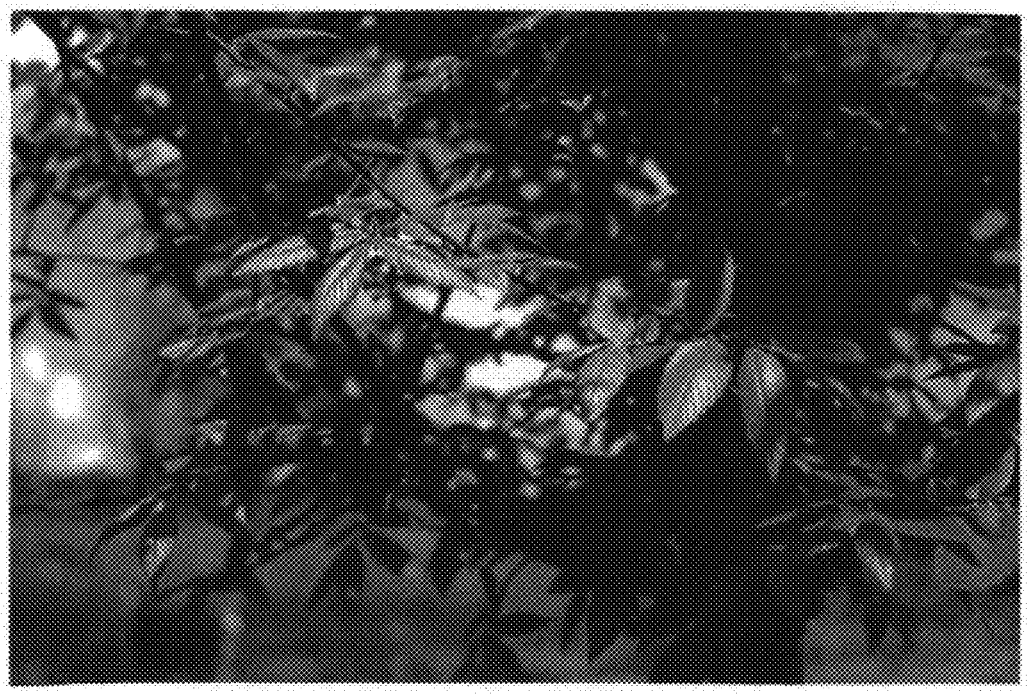
FIG. 4 shows the summer foliage of my new variety.
Figure 5:
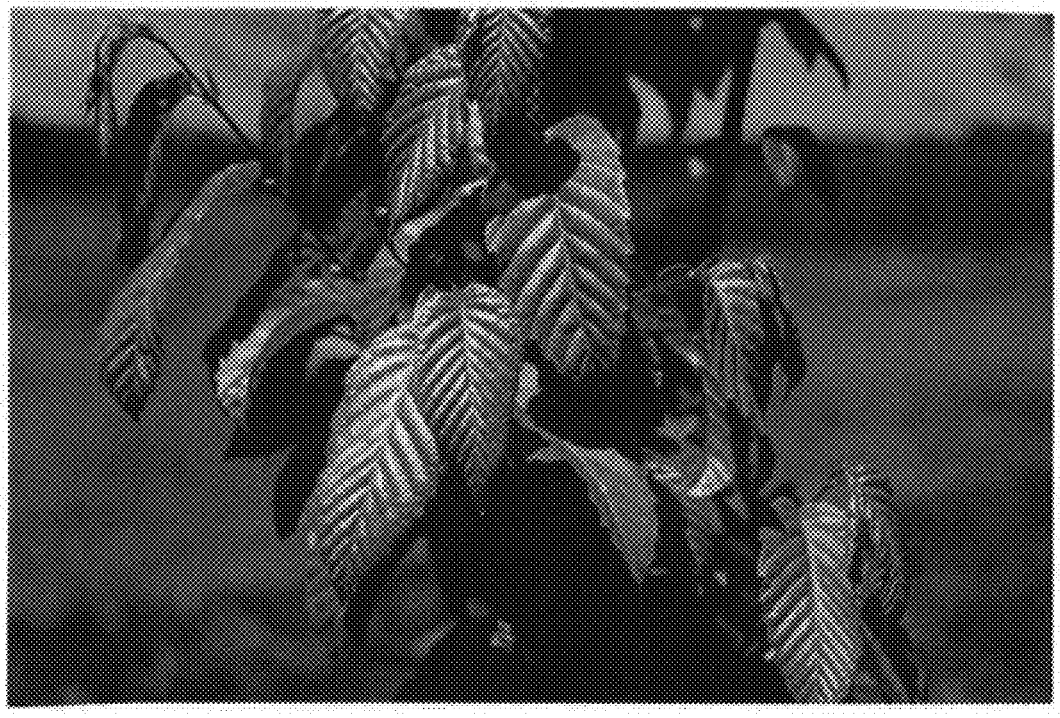
FIG. 5 shows the new growth foliage of my new variety.
Figure 6:
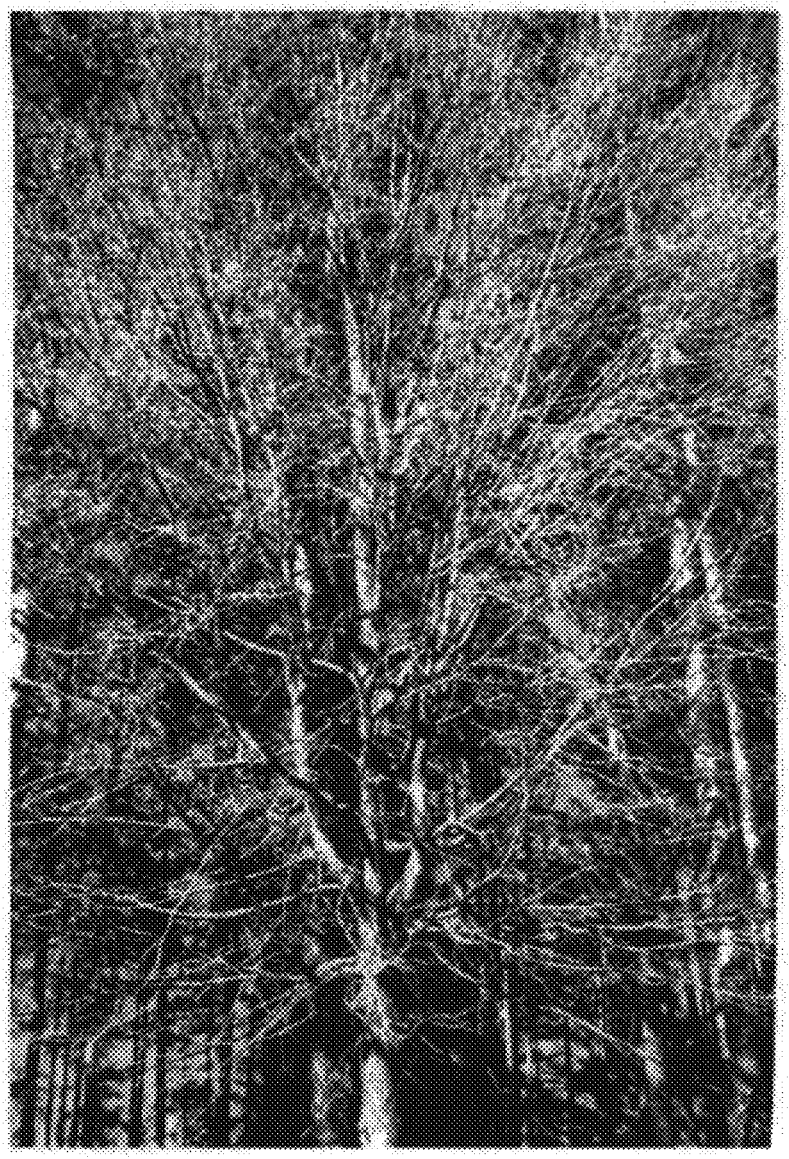
FIG. 6 shows the strong central leader and pyramidal growth habit of my new variety.
Figure 7:
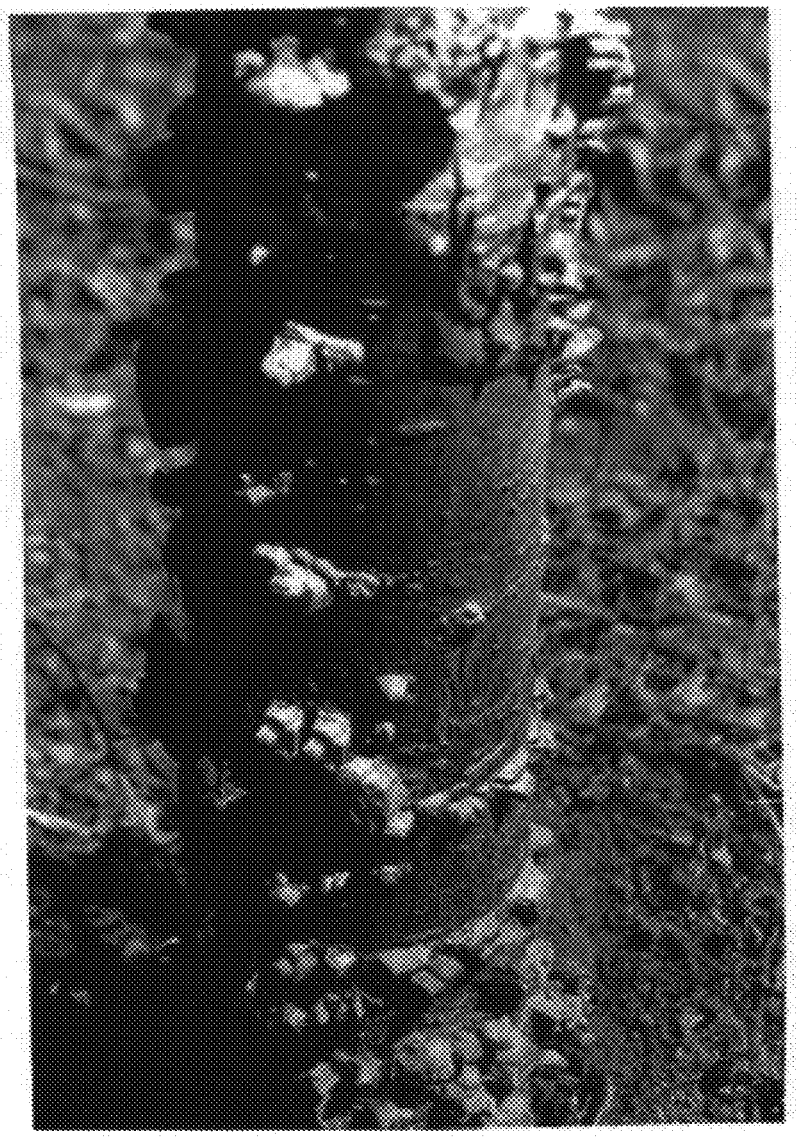
FIG. 7 shows the trunk and bark of my new variety.
Figure 8:
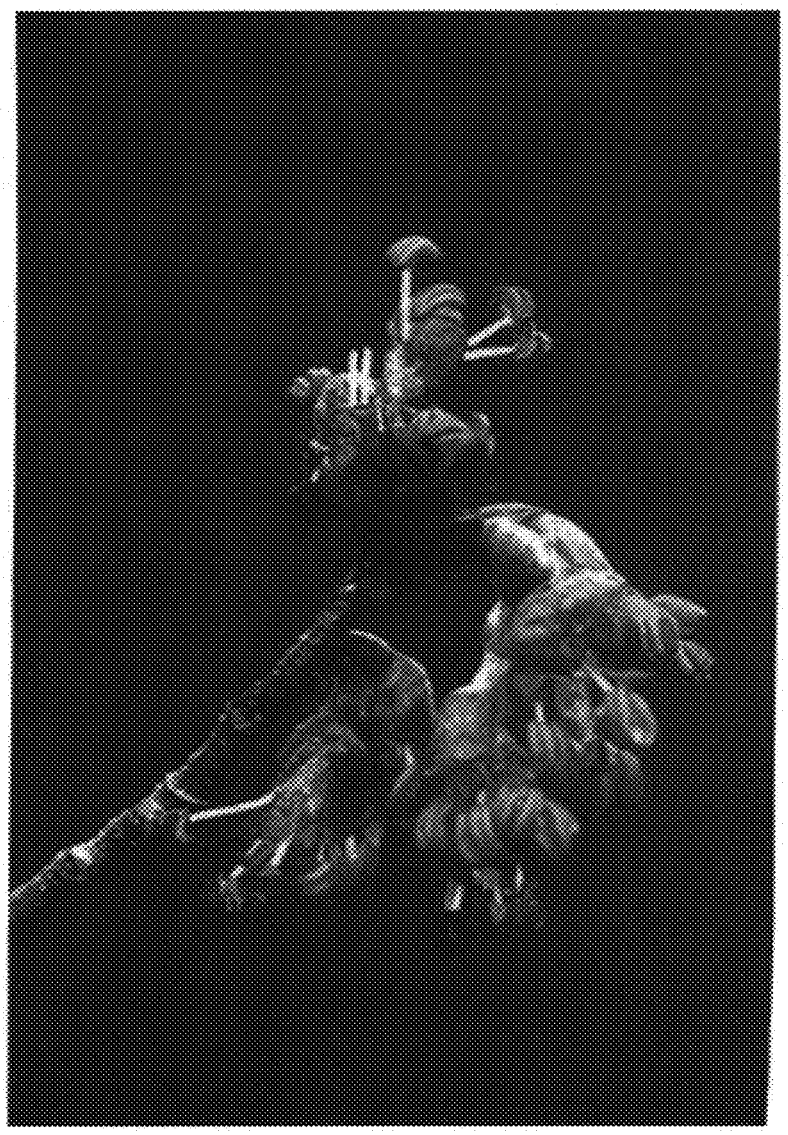
FIG. 8 shows the flower of my new variety.
Figure 9:
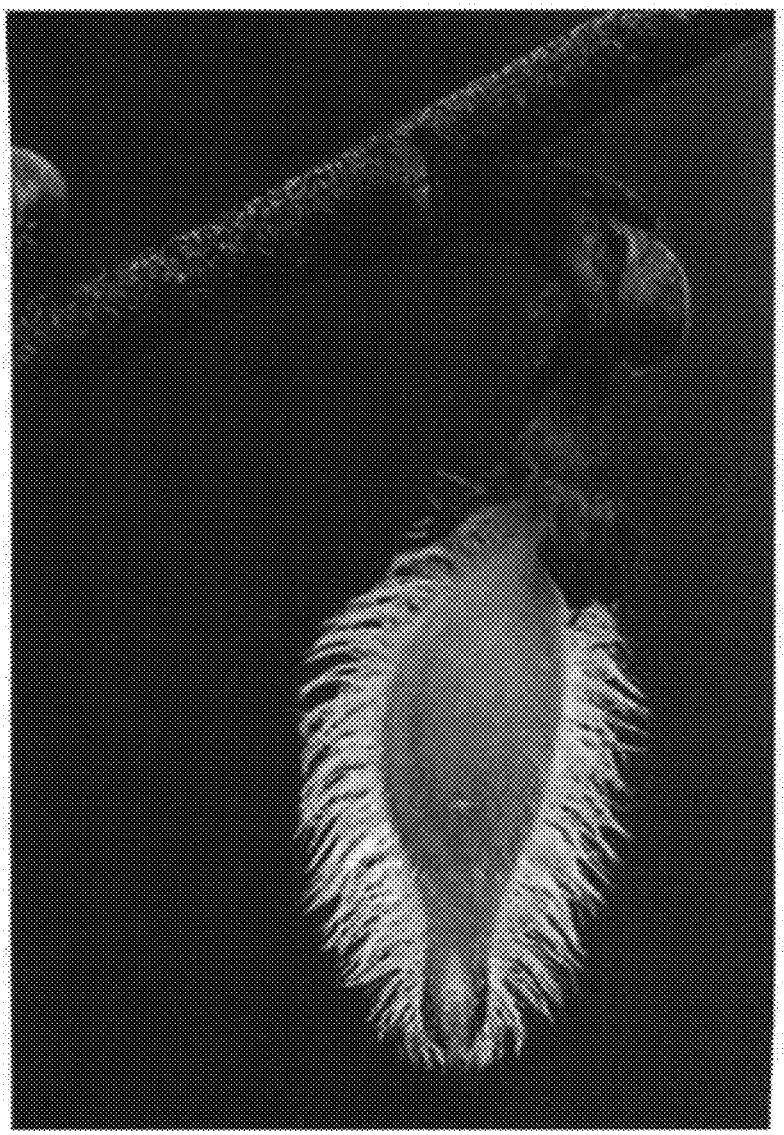
FIG. 9 shows the fruit of my new variety.
Figure 10:
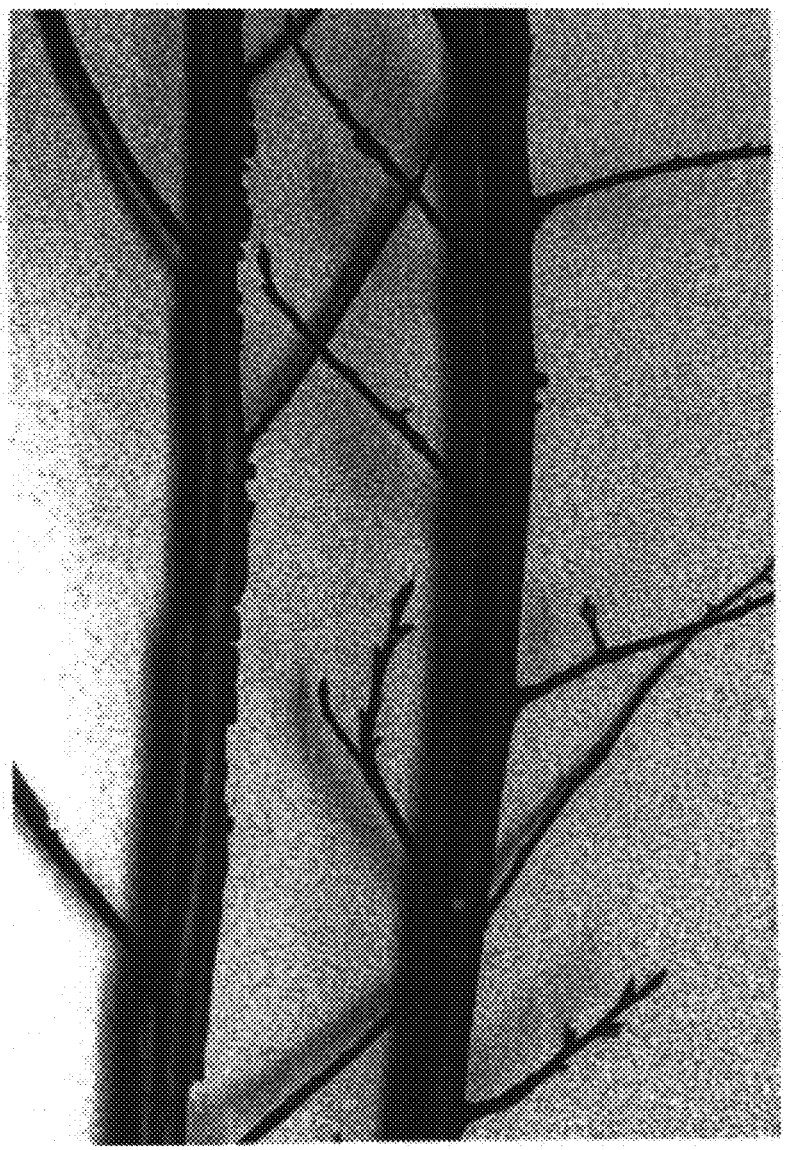
FIG. 10 shows the side by side comparison of the very minimal corky wing-like projections of the claimed cultivar compared to the heavy corky wing-like projections which appear on opposite sides of the branches of the seedling Winged Elm tree.

The following is a detailed description of 'UAMTF' Winged Elm tree with color terminology in accordance with The Royal Horticulture Society (R.H.S.) Colour Chart (2001) except where the context indicates a term having its ordinary dictionary meaning.

The named cultivar has not been observed under all growing conditions, and variations may occur as a result of different growing conditions. All progeny of my new variety, insofar as have been observed by the inventor, have remained genetically stable in all characteristics described hereinafter. Other than as set out hereinafter, as of this time, no other characteristics have been observed by the inventor different from common Winged Elm trees.

Scientific name: *Ulmus alata* 'UAMTP'.

Parentage: Chance discovery by the inventor, Dwayne Moon, of a selection found in the wild in October 2007 from a field in Oconee, Ga.

Propagation:

*Root description.*—The named cultivar is grafted onto seedling rootstocks, so the root system is expected to be typical of the species, which is somewhat coarse.

Tree:

*Growth habit.*—Pyramidal shape with upright branch structure and a strong central leader.

*In a container or in the ground.*—In ground.

*Height.*—Approximately 18 feet at 5 years.

*Plant spread.*—Approximately 10 feet at 5 years.

*Growth rate.*—Height to width ratio 2-1. Average caliper growth rate between ¾ to 1 inch per year.

*Trunk diameter.*—Approximately 4 inch caliper measured at 12 inches above the ground at 5 years. Rises through the canopy and maintains a central leader.

*Trunk bark texture.*—The bark of a young tree has corky wings; the bark of a mature tree has flat plates separated by shallow fissures.

*Branch diameter.*—1.5-2 cm.

*Branch texture.*—Smooth with minimal cork-like wings.

*Branch color.*—Brown like N200A.

Leaves:

*Arrangement.*—Alternate.

*Type.*—Simple.

*Sheen.*—Satiny to slightly glossy.

*Shape of leaf blade.*—Ovate-oblong to oblong-lanceolate.

*Leaf apex shape.*—Acute or acuminate.

*Leaf base shape.*—Cuneate.

*Leaf margin characteristics.*—Doubly-serrate.

*Description of any leaf pubescence.*—Glabrous above with axillary tufts below.

*Leaf length.*—3 cm to 7 cm.

*Leaf width.*—2.5 cm to 3.8 cm.

*Leaf internode length.*—About 2 cm.

*Leaf venation description.*—Pinnate.

*Petiole length.*—About 3 mm.

*Petiole diameter.*—1.5 mm.

*Petiole color.*—Yellow-green like (RHS 146D).

*Petiole texture.*—Pubescent.

*Spring leaf color.*—First emerging leaves are green like (RHS 138B).

*Summer leaf color.*—Upper leaf surface is a dark green foliage like (RHS 137A) while the lower leaf surface is a lighter green foliage like (RHS 137C). The center vein is yellow-green like (RHS 146D).

*Fall color.*—Yellow like (RHS 1A).

Flowers:

*Overall.*—Small, insignificant, greyed red like (RHS 180B), in clusters, appearing March to April before leaf buds open. About 6 mm in length, consisting of a light green calyx with five rounded lobes (up to 9 lobes).

*There are* 4 to 10 *small flowers per cluster which average* 6 *mm in diameter.*

*Shape.*—Pendulous.

*Size.*—Individual flowers have an average diameter of 6 mm.

*Color.*—Greyed-red like (RHS 180B).

*Anthers.*—Greyed purple like (RHS 183B).

*Pistils.*—Greyed green like (RHS 193D).

*Sepals.*—Petal-like lobes, length 0.6 mm, width 0.4 mm, texture fine, margin smooth, color (both surfaces) reddish orange like (RHS 172A).

*Petals.*—Length 1 mm, width 0.5 mm, texture smooth and fine, margin smooth, color (both surfaces) reddish orange like (RHS 172B).

*Stamen.*—About 5 to 9 stamens. Length about 2 mm to 3 mm. Diameter about 0.5 mm. Color: yellow green like (RHS 154B).

*Pollen.*—Yellow like (RHS 10B).

*Pedicel.*—Pedicels are slender. Length: 1.5 cm. Color: yellow green like (RHS 145A).

*Fragrance.*—None.

*Flowering season.*—Flowering in early to late winter to early spring.

*Flower longevity on plant.*—Individual flowers last about 1 to 2 weeks on the plant; flowers not persistent.

Buds:

*Length.*—6 mm.

*Color.*—Greyed red like (RHS 178B).

*Shape.*—Spherical.

Fruit: Flowers replaced by flat, hairy samaras that become mature during mid-spring before vernal leaves fully develop. Samaras about 7 to 10 mm long and about one-half as much across, typically yellow-green like RHS (145C). At tip of each samara, there is a pair of narrow curved claws.

OTHER CHARACTERISICS

Pathogen and pest resistance: Trees of the new *Ulmus alata* have been observed to be resistant to powdery mildew and other leaf-borne illnesses common to *Ulmus alata* trees.

Temperature tolerance: The new *Ulmus alata* is suitable for growing in USDA zones 6 through 9.

The invention claimed is:

1. A new and distinct variety of Winged Elm tree named 'UAMTF' substantially as herein shown, illustrated and described, characterized particularly as to novelty by its strong central leader as well as the refilled, graceful branching which is attained through minimal and insignificant cork-like wings in comparison to the heavy wings evident in seedling Winged Elm, along with its resistance to the powdery mildew and other leaf-borne illnesses found in seedling Winged Elm.

* * * * *